United States Patent [19]

Nakai et al.

[11] Patent Number: 4,514,571
[45] Date of Patent: Apr. 30, 1985

[54] PROCESS FOR THE PREPARATION OF UREA DERIVATIVES

[75] Inventors: Mamoru Nakai; Fumio Iwata; Teruhiko Inoue, all of Ube, Japan

[73] Assignee: UBE Industries, Ltd., Ube, Japan

[21] Appl. No.: 496,179

[22] Filed: May 19, 1983

[30] Foreign Application Priority Data

May 25, 1982 [JP] Japan .................. 57-87276

[51] Int. Cl.$^3$ .............. C07B 29/00; C07C 126/00; C07D 213/89; C07D 263/48
[52] U.S. Cl. ...................... 546/306; 548/233; 548/236; 548/245; 548/246; 548/247; 564/48; 564/58; 564/57; 564/61
[58] Field of Search ............... 546/306; 548/233, 236, 548/245, 246, 247; 564/55, 48, 57, 61

[56] References Cited

U.S. PATENT DOCUMENTS 3,935,258  1/1976  Hempel et al. .................. 71/120

Primary Examiner—Henry R. Jiles
Assistant Examiner—Dale A. Bjorkman
Attorney, Agent, or Firm—Frishauf, Holtz, Goodman & Woodward

[57] ABSTRACT

A process for the preparation of a urea derivative having the formula:

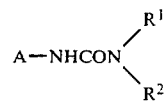

in which A represents a straight- or branched-chain alkyl group having 1–20 carbon atoms, an aryl group, or a heterocyclic group, and each of $R^1$ and $R^2$ represents hydrogen, a straight- or branched-chain alkyl group having 1–20 carbon atoms, an alicyclic group, or an aryl groups, which comprises:
reacting sodium salt of an N-halogenamide with a quaternary ammonium salt to obtain its addition salt and then,
reacting said addition salt with an amine derivative in the absence or presence of an organic solvent.

7 Claims, No Drawings

PROCESS FOR THE PREPARATION OF UREA DERIVATIVES

This invention relates to a process for the preparation of a urea derivative, and in particular relates to a process for the preparation of a urea derivative starting from an acid amide.

A variety of urea derivatives are known and some of these urea derivatives are of value as pesticides, particularly herbicides, and intermediate compounds for preparations of pharmaceuticals.

The urea derivative is obtained in good yield by the addition reaction between an alkylisocyanate or arylisocyanate and an amine. However, this process is disadvantageous because the isocyanate is so instable that the preparation thereof is not easy. More in detail, the isocyanate can be prepared from an acid amide in the following stages: the acid amide is, in the first place, N-halogenated in an aqueous sodium hypochlorite solution and decomposed under rearrangement in an aqueous alkaline solution to prepare an amine; and the so prepared amine is reacted with phosgene to obtain an isocyanate. As is easily understood from the description of these stages, the process for the preparation of an isocyanate from an acid amide is disadvantageous in requiring long and complicated reaction stages and in employing toxic phosgene.

Accordingly, a primary object of the present invention is to provide an improved process for the preparation of a urea derivative.

The present invention resides in a process for the preparation of a urea derivative having the formula (I):

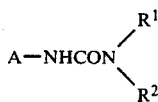

in which A represents a straight- or branched-chain alkyl group having 1-20 carbon atoms, an aryl group, or a heterocyclic group, and each of $R^1$ and $R^2$ represents hydrogen, a straight- or branched-chain alkyl group having 1-20 carbon atoms, an alicyclic group, or an aryl groups, which comprises:

reacting sodium salt of an N-halogenamide having the formula:

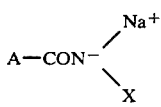

in which A is the same as above, and X represents halogen, with a quaternary ammonium salt to obtain its addition salt having the formula:

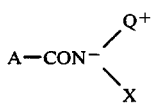

in which A and X are the same as above, and Q represents a quaternary ammonium, and then,
reacting said addition salt with an amine derivative having the formula:

in which each of $R^1$ and $R^2$ is the same as above, in the absence or presence of an organic solvent.

The present invention is described hereinbelow in detail.

The urea derivative prepared by the present invention has the formula (I):

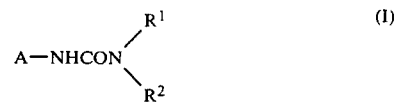

In the formula (I), A represents a straight- or branched-chain alkyl group having 1-20 carbon atoms, preferably 1-8 carbon atoms, such as methyl, ethyl, n-propyl, isopropyl, n-butyl, isobutyl, pentyl, hexyl, heptyl, or octyl; an aryl group preferably having 6-12 carbon atoms such as phenyl, toluyl, or xylyl; or a heterocyclic group such as pyridyl, picolyl, oxazolyl, and isoxazolyl.

$R^1$ and $R^2$ are the same or different, and each represents hydrogen, a straight- or branched-chain alkyl group having 1-20 carbon atoms, preferably 1-8 carbon atoms, such as methyl, ethyl, n-propyl, isopropyl, n-butyl, isobutyl, pentyl, hexyl, heptyl, or octyl; an alicyclic group preferably having 5-6 carbon atoms such as cyclopentyl, or cyclohexyl, or an aryl group preferably having 6-12 carbon atoms phenyl, toluyl, or xylyl.

In the first stage of the process of the invention, sodium salt of an N-halogenamide having the formula (II):

in which A is the same as above, and X represents halogen such as chlorine or bromine, is reacted with a quaternary ammonium salt to obtain its addition salt having the formula (III):

in which A and X are the sme as above, and Q represents a quaternary ammonium.

An N-halogenamide having the formula (II) can be prepared, in a known manner, namely, by reacting an acid amide in an aqueous sodium hypochlorite solution in the presence of sodium hydroxide.

In the above-described reaction, the quaternary ammonium salt generally is a tetraalkylammonium halide having four same or different alkyl groups of 1-18 carbon atoms and is preferably selected from the group consisting of trioctylmethylammonium chloride, trioctylmethylammonium bromide, tetrabutylammonium chloride, tetrabutylammonium bromide, lauryltrimethylammonium chloride, lauryltrimethylammonium bromide, octyltrimethylammonium chloride, and octyltrimethylammonium bromide.

The reaction is preferably carried out at a temperature of from 0° to 30° C.

In the second stage, the addition salt having the formula (III) is reacted with an amine derivative having the formula (IV):

(IV)

in which each of $R^1$ and $R^2$ is the same as above, in the absence or presence of an organic solvent.

The said amine derivative having the formula (IV) is ammonia, a primary amine or a secondary amine, and is preferably selected from the group consisting of ammonia, methylamine, ethylamine, propylamine, butylamine, cyclopentylamine, cyclohexylamine, aniline, dimethylamine, diethylamine, dibutylamine, and methylbutylamine.

As mentioned above, the reaction of the second stage can be carried out in an organic solvent. The organic solvent preferably is an aromatic organic solvent such as benzene, toluene or xylene.

The reaction of the second stage can be carried out at a temperature of from 50° to 100° C., preferably from 70° to 90° C. The reaction period generally ranges from about 20 to 90 min. The amine derivative is generally employed in a molar ratio of from 1.0 to 30, preferably from 1.1 to 3, against one mole of the addition salt having the aforementioned formula (III)

In the reaction of the second stage, a quaternary ammonium salt is obtained as a by-product, which can be cycled for the use in the next first stage reaction.

The present invention is further described by the following examples.

EXAMPLE 1

In a reaction vessel were successively placed 9.42 g. (11 mmol.) of 8.7% NaOCl, 1.36 g. (17 mmol.) of 50% NaOH, and 1.8432 g. (purity 91.32%, 10 mmol.) of 5-t-butyl-3-isoxazolylcarboxamide. The mixture was stirred for 60 min. under cooling with cold water to keep the temperature of the mixture below 18° C. When the stirring was complete, the mixture became to a homogeneous solution.

3.25 g. (10.1 mmol.) of tetrabutylammonium bromide was added to the so obtained reaction solution to separate an oily reaction product from the solution. The solution was then stirred for 20 min. and extracted with two portions of 50 ml. of methylene chloride. The methylene chloride extract was concentrated. The obtained concentrate, as well as 100 ml. of toluene containing 4.6 g. (148 mmol.) of methylamine, was placed in a glass autoclave. The mixture was heated therein under stirring at 85° C. for 90 min. An excess of the methylamine was removed under the influence of heat of the reaction mixture, and the mixture was cooled to room temperature.

After being cooled, a part of the reaction mixture was taken out to analyze on HLC. There was found that N-methyl-N'-(5-t-butyl-3-isoxyazoyl)urea was obtained in the amount of 1.8833 g. (9.55 mmol.); yield 95.50%.

The remaining portion was extracted with two portions (30 ml. and 15 ml., respectively) of water in a separating funnel to recover tetrabutylammonium chloride. It was confirmed that the so obtained aqueous extract was employable cyclically for a next reaction.

EXAMPLES 2-7

The procedures of Example 1 were repeated except that methylamine was replaced with ethylamine (Example 2), propylamine (Example 3), butylamine (Example 4), cyclopentylamine (Example 5), cyclohexylamine (Example 6), and aniline (Example 7), respectively.

In Example 2, N-ethyl-N'-(5-t-butyl-3-isoxyazoyl)urea was obtained in 96.20% yield.

In Example 3, N-propyl-N'-(5-t-butyl-3-isoxyazoyl)urea was obtained in 94.10% yield.

In Example 4, N-butyl-N'-(5-t-butyl-3-isoxyazoyl)urea was obtained in 93.12% yield.

In Example 5, N-cyclopentyl-N'-(5-t-butyl-3-isoxyazoyl)urea was obtained in 92.2% yield.

In Example 6, N-cyclohexyl-N'-(5-t-butyl-3-isoxyazoyl)urea was obtained in 95.30% yield.

In Example 7, N-phenyl-N'-(5-t-butyl-3-isoxyazoyl)urea was obtained in 93.8% yield.

EXAMPLES 8-10

The procedures of Example 3 were repeated except that tetrabutylammonium bromide was replaced with lauryltrimethylammonium chloride (Example 8), octyltrimethylammonium chloride (Example 9), and trioctylmethylammonium chloride (Example 10), respectively.

There were obtained N-propyl-N'-(5-t-butyl-3-isoxyazoyl)urea was obtained in yields of 85.40% (Example 8), 83.10% (Example 9), and 95.70% (Example 10), respectively.

EXAMPLES 11-13

The procedures of Example 1 were repeated except that methylamine was replaced with dimethylamine (Example 11), diethylamine (Example 12), and butylmethylamine (Example 13), respectively.

In Example 11, N,N-dimethyl-N'-(5-t-butyl-3-isoxyazoyl)urea was obtained in 93.82% yield.

In Example 12, N,N-diethyl-N'-(5-t-butyl-3-isoxyazoyl)urea was obtained in 94.30% yield.

In Example 13, N-butyl-N-methyl-N'-(5-t-butyl-3-isoxyazoyl)urea was obtained in 92.20% yield.

EXAMPLE 14

In a reaction vessel were successively placed 9.41 g. (11 mmol.) of 8.7% NaOCl, 1.36 g. (17 mmol.) of 50% NaOH, and 1.2220 g. (10 mmol.) of nicotinamide. The mixture was stirred for 60 min. under cooling with cold water to keep the temperature of the mixture at 5°-7° C. The nicotinamide was dissolved within 5-6 min.

4.06 g. (10 mmol.) of trioctylmethylammonium chloride was added to the so obtained reaction solution, and the mixtue was then stirred for 20 min. 100 ml. of toluene was added to the reaction mixture, and the toluene layer was separated. To the toluene layer was added 3.01 g. (51.0 mmol.) of propylamine, and the mixture was placed in a glass autoclave. The mixture was heated therein under stirring at 90° C. for 60 min. An excess of propylamine was removed under the influence of heat of the reaction mixture, and the mixture was cooled to room temperature.

After being cooled, the reaction mixture was extracted with two 50 ml. portions of water, and the aqueous extract was analyzed on HLC. There was found that N-propyl-N'-(β-pyridyl)urea was obtained in the amount of 1.2987 g. (7.25 mmol.); yield 72.5%.

EXAMPLE 15

The procedures of Example 14 were repeated except that nicotinamide was replaced with α-picolinamide to give N-propyl-N'-(α-pyridyl)urea in 71.1% yield.

EXAMPLE 16

The procedures of Example 1 were repeated except that (5-t-butyl-3-isooxazoyl)formamide and methylamine were replaced with benzamide and dimethylamine, respectively, to give N,N'-dimethyl-N'-phenylurea in 64.70% yield.

EXAMPLE 17

The procedures of Example 1 were repeated except that 5-t-butyl-3-isoxazolylcarboxamide and methylamine were replaced with n-butyramide and aniline, respectively, to give N-propyl-N'-phenylurea in 46.70% yield.

We claim:

1. A process for the preparation of a urea derivative having the formula:

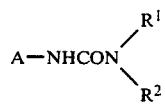

in which A represents a straight- or branched-chain alkyl group having 1–20 carbon atoms, an aryl group, or a heterocyclic group, and each of $R^1$ and $R^2$ represents hydrogen, a straight- or branched-chain alkyl group having 1–20 carbon atoms, an alicyclic group, or an aryl groups, which comprises:

reacting sodium salt of an N-halogenamide having the formula:

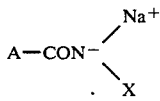

in which A is the same as above, and X represents halogen, with a quaternary ammonium salt to obtain its addition salt having the formula:

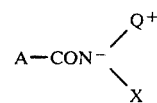

in which A and X are the same as above, and Q represents a quaternary ammonium, and then, reacting said addition salt with an amine derivative having the formula:

in which each of $R^1$ and $R^2$ is the same as above, in the absence of a solvent or presence of an organic solvent.

2. The process for the preparation of the urea derivative as claimed in claim 1, in which A is a group selected from the group consisting of a straight- or branched-chain alkyl group having 1–8 carbon atoms, an aryl group having 6–12 carbon atoms, pyridyl group, picolyl group, oxazolyl group, and isoxazolyl group.

3. The process for the preparation of the urea derivative as claimed in claim 1, in which said quaternary ammonium salt is a tetraalkylammonium halide having four same or different alkyl groups of 1–18 carbon atoms.

4. The process for the preparation of the urea derivative as claimed in claim 3, in which said tetraalkylammonium halide is selected from the group consisting of trioctylmethylammonium chloride, trioctylmethylammonium bromide, tetrabutylammonium chloride, tetrabutylammonium bromide, lauryltrimethylammonium chloride, lauryltrimethylammonium bromide, octyltrimethylammonium chloride, and octyltrimethylammonium bromide.

5. The process for the preparation of the urea derivative as claimed in claim 1, in which each of $R^1$ and $R^2$ represents hydrogen, a straight- or branched-chain alkyl group having 1–8 carbon atoms, an alicyclic group having 5–6 carbon atoms, or an aryl group having 6–12 carbon atoms.

6. The process for the preparation of the urea derivative as claimed in claim 1, in which said amine derivative is selected from the group consisting of ammonia, methylamine, ethylamine, propylamine, butylamine, cyclopentylamine, cyclohexylamine, aniline, dimethylamine, diethylamine, dibutylamine, and methylbutylamine.

7. The process for the preparation of the urea derivative as claimed in claim 1, in which the reaction between said addition salt with said amine derivative is carried out in an aromatic organic solvent.

* * * * *